(12) United States Patent
Hayakawa et al.

(10) Patent No.: US 6,919,043 B2
(45) Date of Patent: Jul. 19, 2005

(54) METHOD OF STERILIZATION FOR CONTAINER, APPARATUS USING THEREFOR AND HEAT TREATMENT FOR CONTAINER

(75) Inventors: Atsushi Hayakawa, Tokyo-to (JP); Makoto Hayashi, Tokyo-to (JP); Masatoshi Takagi, Tokyo-to (JP); Akira Koyama, Tokyo-to (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 56 days.

(21) Appl. No.: 10/074,359

(22) Filed: Feb. 12, 2002

(65) Prior Publication Data

US 2003/0165400 A1 Sep. 4, 2003

(51) Int. Cl.⁷ .................................................. A61L 2/22
(52) U.S. Cl. ........................ 422/28; 422/302; 422/303; 422/304
(58) Field of Search ................................. 422/3, 28, 32, 422/300, 302, 303, 304, 305, 307; 53/425, 426, 486

(56) References Cited

U.S. PATENT DOCUMENTS

| | | | | |
|---|---|---|---|---|
| 5,308,233 A | * | 5/1994 | Denis et al. | 425/151 |
| 5,368,828 A | * | 11/1994 | Carlson | 422/300 |
| 5,879,648 A | * | 3/1999 | Hada et al. | 422/304 |
| 6,209,591 B1 | * | 4/2001 | Taggart | 141/89 |
| 2002/0085971 A1 | * | 7/2002 | Raniwala | 422/303 |
| 2002/0159915 A1 | * | 10/2002 | Zelina et al. | 422/3 |
| 2003/0068251 A1 | * | 4/2003 | Smith et al. | 422/28 |

FOREIGN PATENT DOCUMENTS

DE 4212433 * 10/1993

* cited by examiner

Primary Examiner—E. Leigh McKane
(74) Attorney, Agent, or Firm—Ladas & Parry LLP

(57) ABSTRACT

At the step of preheating the container, in addition to heating of the whole container, a neck portion (1a) of the container may be heated separately. Alternatively on the step of preheating the container, while whole container is heated by a hot air blast which is supplied in the container, neck portion (1a) of the container may be heated separately. Since it is difficult to increase the temperature of the neck portion as compared with other portions, by heating the neck portion separately, the effect of the preheating is performed more effectively. It is desirable that the hot air blast is supplied from the nozzle inserted in the container. For example by the method of spraying hot air blast from the outside of the portions, heating of the neck portions can be performed.

6 Claims, 5 Drawing Sheets

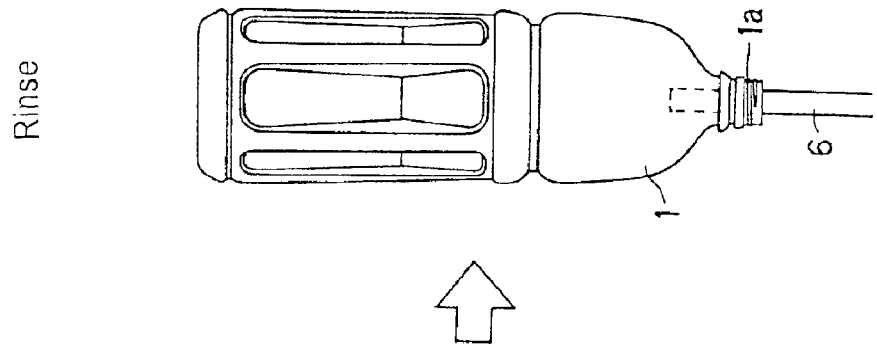
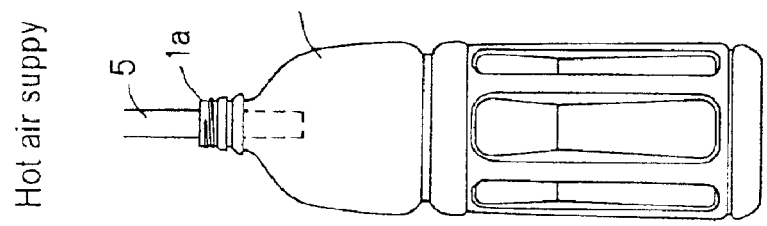
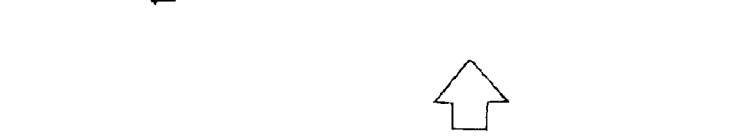
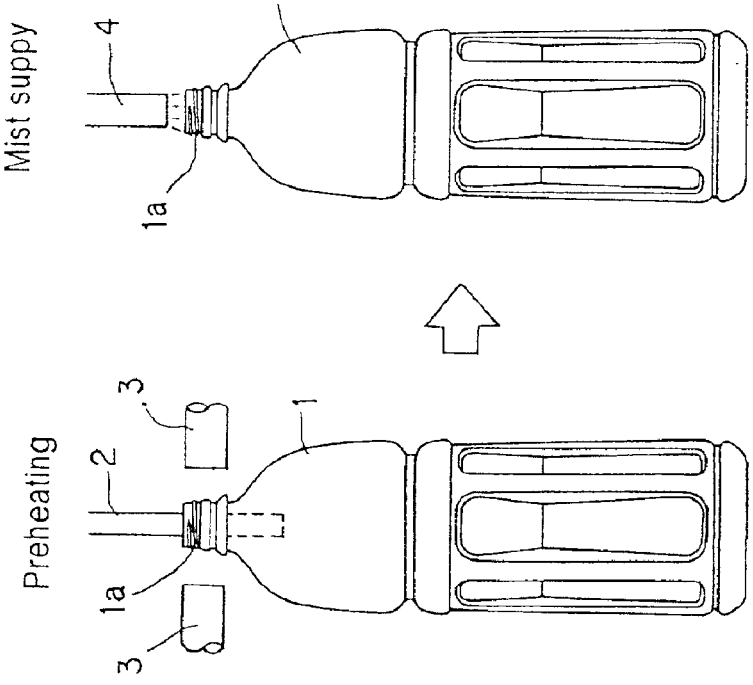

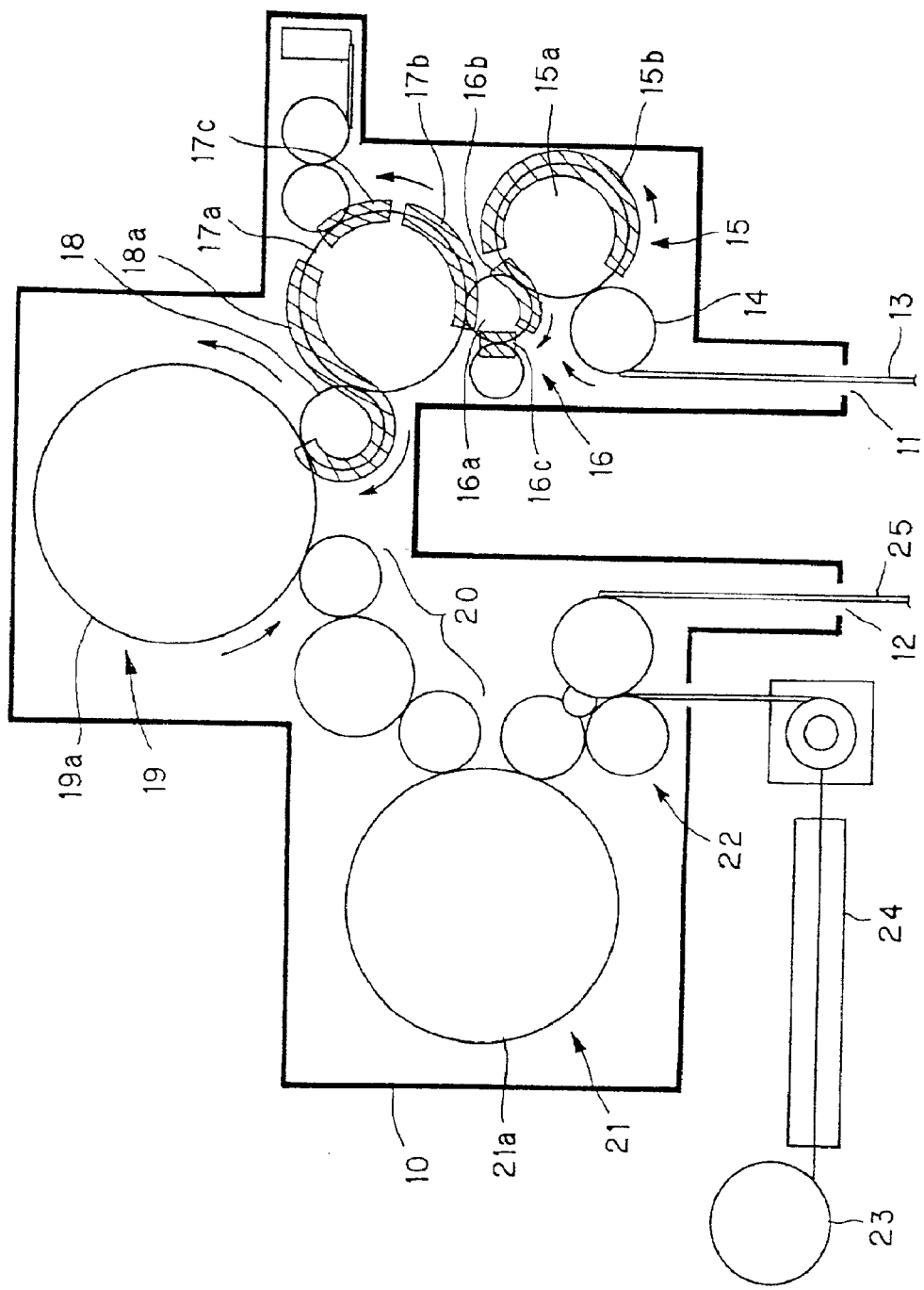

METHOD OF STERILIZATION FOR CONTAINER, APPARATUS USING THEREFOR AND HEAT TREATMENT FOR CONTAINER

BACKGROUND OF THE INVENTION

1. Field of the Invention

This invention relates to the method of sterilization for containers, such as a beverage bottle, and apparatus using the same.

2. Related Art

The method for sterilizing containers such as a bottle applied to an aseptic packaging machine, is known. For example, Japanese Patent No. 2851373 discloses the method which sterilizes peracetic-acid aqueous solution and hydrogen peroxide by spraying in containers. Moreover, JP-A-3-224469 discloses the method which comprises heating of hydrogen peroxide sprayed into the chamber, which is followed by evaporation of the heated hydrogen peroxide, condensing thereof in air which is followed by forming of germicide mist, contacting this mist in a container which is followed by sterilizing for the container.

SUMMARY OF THE INVENTION

There is an inline system as aseptic packaging system of such as the PET bottle. This system is consistently done on the line which is identical from the molding of the bottle to the filling the bottle with contents. In this system, about per minute 500–1000 throughputs are desired, and in order to attain this, shortening the time of sterilization for the bottle has made to be a technical problem. The conventional method of spraying hydrogen peroxide solution has the enough sterilizing activity, because the high-concentration hydrogen peroxide is used. However, in this method, it is not possible to shorten, because a hydrogen peroxide adsorbs and permeates to the surface layer of the container made of the plastic, and that the hydrogen peroxide is removed from the surface layer taking labor.

An object of the invention is to provide the method which can sterilize various containers at high speed and certainly, the apparatus suitable for the method, and heat treatment for container.

Hereafter, this invention is described. Although the reference mark of an annexed drawing is written in addition in parenthesis writing in order to make understanding of this invention easy, thereby, this invention is not limited to the embodiments as illustrated.

The method for sterilizing a container of this invention solves the technical problem mentioned above by comprising the steps of: supplying a disinfectant mist into a container(1); heating the container into which the mist has been supplied, while discharging the mist from the container; and rinsing an inside of the container after discharge of the mist therefrom.

Since disinfectant mist is formed by condensed disinfectant drop which is once evaporating, its concentration is high and It can carry out the sterilization with efficient. By heating the container after supplying a disinfectant mist, the sterilization effect improves, penetration of a disinfectant component into the container is suppressed, and the disinfectant component becomes easy to appear on the surface of a container. And by discharging the mist which is drifting to the internal space of the container, seen from the field of the sterilization effect, adsorption of the surplus disinfectant into inner surface of the container is prevented, and penetration of the disinfectant into the container can be suppressed still effectively. And by rinsing an inside of the container after discharge of the mist therefrom, the disinfectant which is absorbed and penetrated into the container is flushed, and the residual concentration of the disinfectant is reduced to the degree of minimum.

The sterilization method of this invention may comprise a further step of preheating the container in advance of supply of the mist. By preheating, from the beginning the mist supply, the high sterilization effect is performed the container, and it can sterilize efficiently for a short time. Penetration of the disinfectant into the container can be suppressed more effectively.

At the step of preheating the container, in addition to heating of the whole container, a neck portion (1a) of the container may be heated separately. Alternatively on the step of preheating the container, while whole container is heated by a hot blast which is supplied in the container, the neck portion (1a) of the container may be heated separately. Since it is difficult to increase the temperature of the neck portion as compared with other portions, by heating the neck portion separately, the effect of the preheating is performed more effectively. It is desirable that the hot blast is supplied from the nozzle Inserted In the container. For example by the method of spraying hot blast from the outside of the neck portions, heating of the neck portions can be performed.

After supplying a disinfectant mist, before starting to discharge the mist from the container, the sterilization method of this invention may comprise a further step of providing a prescribed leaving time. By providing a prescribed leaving time, the mist is evenly contacted to the inner surface of the container, and the inner surface of the container is surely sterilized. Incidentally, providing a prescribed leaving time can also serve as a conveyance time of the container from the step of supplying the mist to the step of discharging the mist.

After discharging the mist, before starting to rinse an inside of the container, the sterilization method of this invention may comprise a further step of providing a prescribed standing a time. By providing a prescribed standing a time, the disinfectant is surely appeared on the surface of the container, and a rinsing effect can be raised. Providing a prescribed standing a time can also serve as a conveyance time of the container from the step of discharging the mist to the step of rinsing.

In the sterilization method of this invention, hot blast is supplied in the container which was supplied the mist, and heating of the container and discharging the mist may be performed. If it does in this way, discharging the mist and heating the container can be performed efficiently.

At the step of rinsing inside of the container, rinsing fluid heated in advance can be supplied into the container. By rinsing fluid heated in advance, the heat promotes the disinfectant appearing on the surface of the container, and a high rinsing effect can be performed.

The apparatus for sterilizing a container of this invention solved the technical problem mentioned above by comprising a device for supplying a disinfectant mist into a container (1)(16); a device for heating the container (1) into which the mist has been supplied (17); a device for discharging the mist from the container (17); and a device for rinsing an inside of the container from which the mist has been discharged (19).

Alternatively, the apparatus for sterilizing a container of this invention solved the technical problem mentioned above may comprise a device for supplying a disinfectant mist into a container (1)(16); a device for supplying a hot blast into the container (1) into which the mist has been supplied(17); and a device for rinsing an inside of the container(19).

According to these apparatuses, since a disinfectant mist is supplied into the container, the container into which the mist has been supplied is heated, while the mist is discharged from the container, and the container of which the mist has been discharged is rinsed, the method The method for sterilizing a container of this invention is realizable.

The apparatus for sterilizing a container of this invention, may comprise a further device for preheating the container in advance of supply of the mist. As the device for preheating, the device for heating whole container by hot blast which is supplied in the container, and the device for heating the lip portion of the container may be comprise. As the device for rinsing, the device for supplying the rinsing fluid heated may be comprise. It is desirable that the hot blast is supplied from the nozzle inserted in the container.

Furthermore, the heat treatment of the container of this invention is characterized by while heating the whole container by hot blast which is supplied from the nozzle inserted in the container (1), the neck portion (1a) of the container is heated separately.

By this treatment, the hot blast is surely supplied in the container by the nozzle inserted in the container. Moreover by heating the neck portion separately, which is more difficult to increase the temperature of, the whole container can be surely and quickly heated to desired temperature. Therefore, it this heat treatment is applied at the step of preheating in the sterilization method of this Invention, it can contribute to improvement In the speed of the sterilization processing. In addition, the heat treatment for the container of this invention can be used not only the preheating of the sterilization processing of the container, but all cases in which the heating of the container is needed.

BRIEF DESCRIPTION OF THE DRAWINGS

FIG. 1 is a schematic view showing a step of sterilization for a beverage bottle of the an embodiment of the present invention;

FIG. 4 is a plan view showing an aseptic packaging system of an embodiment of the present invention.

DETAILED DESCRIPTION OF THE PREFERRED EMBODIMENTS

Figure 2:
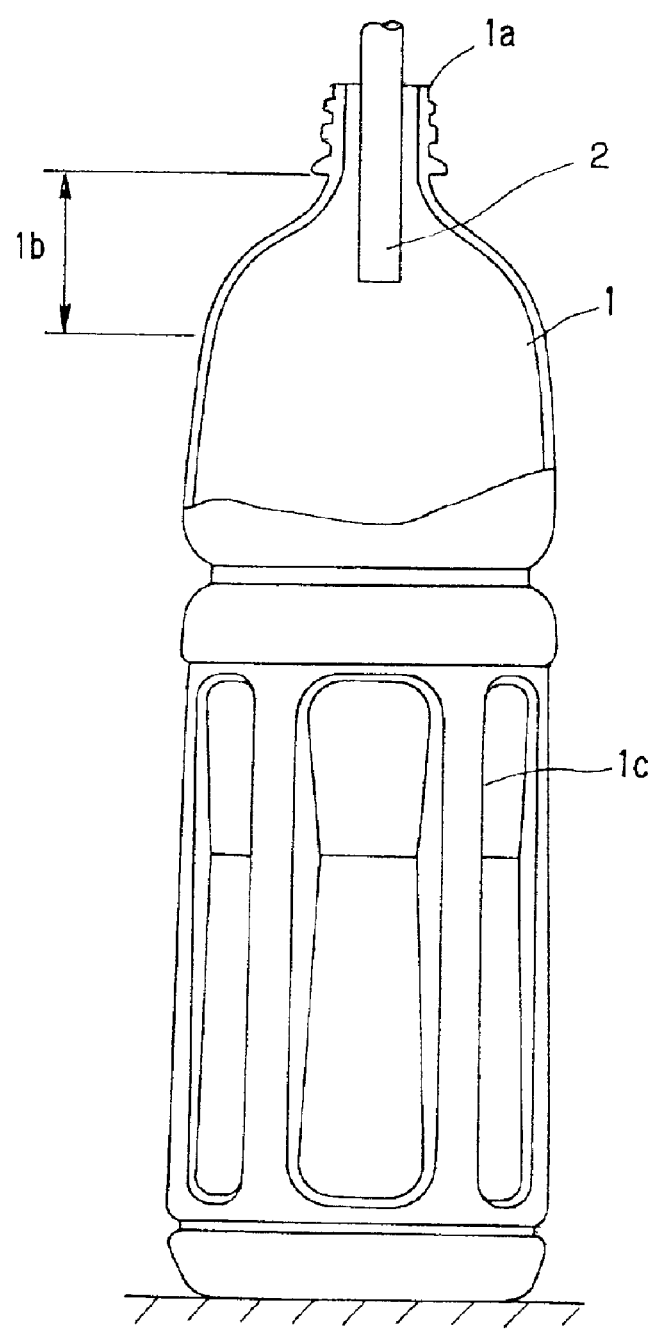
FIG. 2 is a view showing the condition that the nozzle was inserted in the bottle.

FIG. 1 shows a schema of the step of sterilization for a beverage bottle of an embodiment of the present invention, By this sterilization method, as first shown in FIG. 1(a), a nozzle 2 is inserted in the interior from a neck portion 1a of a bottle 1, hot blast is supplied in from the nozzle 2, and the bottle 1 is preheated. Simultaneously, nozzles 3 and 3 are set in the periphery of the neck portion 1a of the bottle 1, hot blast is sprayed on the neck portion 1a from those nozzles 3, and the neck portion 1a is heated further, because there is a possibility that the neck portion 1a may not fully be heated only by the hot blast from a nozzle 2. When the neck portion 1a can fully be heated only by the hot blast from a nozzle 2, it is possible to omit the nozzles 3. To insert the nozzle 2 in the bottle 1 is for surely supplying the hot blast in the bottle 1. Although the amount of insertions of a nozzle 2 may be suitably changed according to the flow rate of hot blast, the aperture of the neck portion 1a, etc., as shown in FIG. 2, it is good that the top of the nozzle 2 is set at a transition region 1b of a diameter of the bottle which is set between the neck portion 1a of the bottle and a body of the bottle. The transition region 1b can be defined as the range in which the bottle diameter expands from the lower end of the neck portion 1a of the bottle to 70% of the largest diameter for example. It is desirable that the preheating is carried out so that the inner surface of the bottle 1 may become over 40° C.

Figure 3:
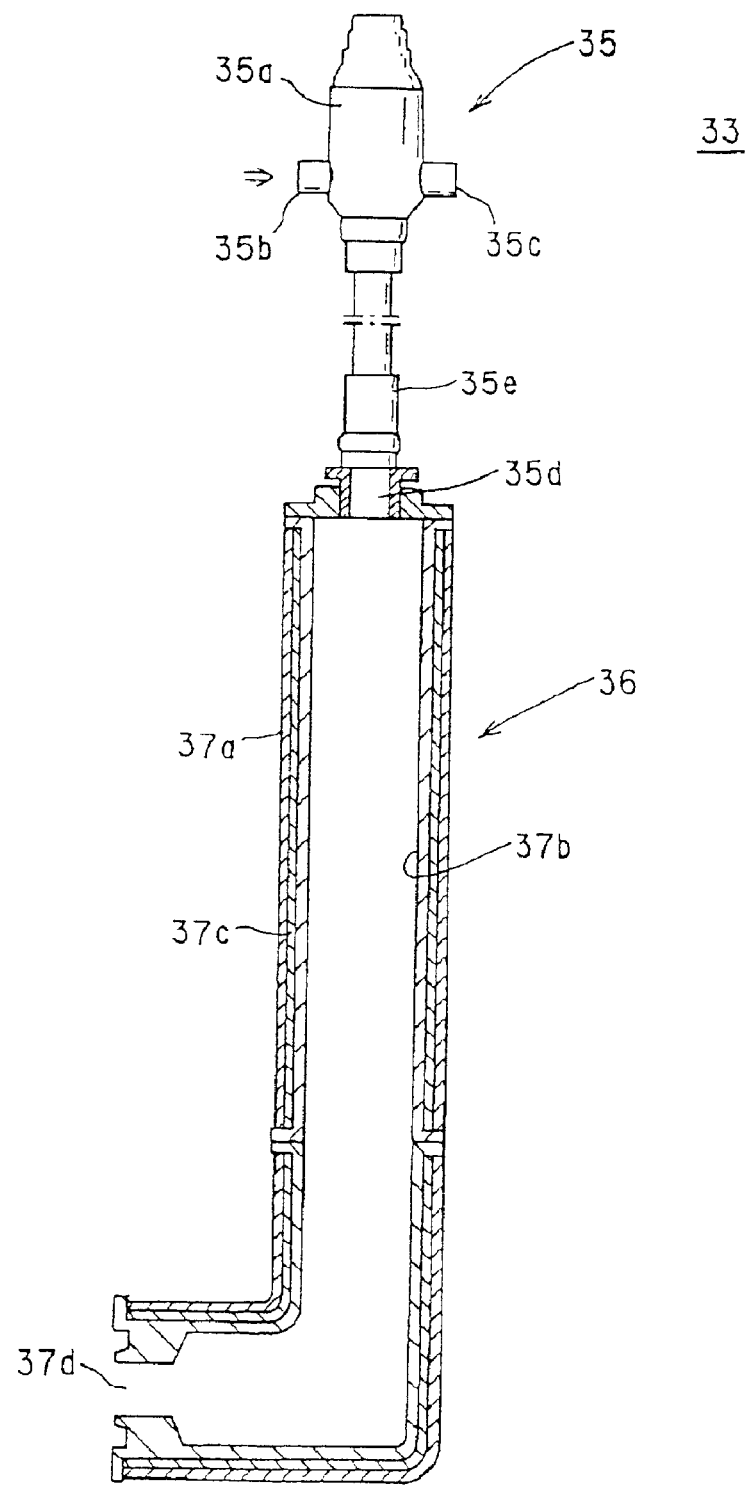
FIG. 3 is a view showing the apparatus to form a disinfectant mist.

The preheated bottle 1 is carried to a step of supplying a mist. At the step of supplying a mist, a disinfectant mist is supplied into of the bottle 1 from a nozzle 4. The disinfectant mist is formed by a mist-generator 33 shown in FIG. 3. This generator 33 comprises of the disinfectant supply section 35 which forms a guttatus aqueous solution of hydrogen peroxide ($H_2O_2$) and supplies it, and evaporating section 36 which heats the aqueous solution of hydrogen peroxide ($H_2O_2$) supplied this disinfectant supply section 35, and evaporates it more than the boiling point. A spray 35a is prepared in the disinfectant supply section 35. A disinfectant supply port 35b and a compressed-air supply port 35c are prepared in the spray 35a. These ports 35b, 35c, respectively, are connected the hydrogen peroxide supply source or the compressed-air supply source which is not shown.

Since the aqueous solution of a hydrogen peroxide and the compressed-air which are supplied from the supply ports 35b, 35c are mixed inside the double fluid spray 35a, the aqueous solution of a hydrogen peroxide is sprayed in a evaporation tube 37 of the evaporating section 36 from a nozzle 35d connected through the spray 35a and extension pipe 35e. For example, the evaporation tube 37 has the external cylinder 37a which consists of an asbestos ribbon, the inner cylinder 37b which consists of the sanitary pipe which forms the inner wall of the evaporation tube 37, and the heater 37c as a device for heating which is set between the external cylinder 37a and the inner cylinder 37b. The nozzle 4 mentioned above is connected with a discharge opening 37d of a bottom of the evaporation tube 37.

The guttatus aqueous solution of hydrogen peroxide which is supplied into the evaporation tube 37, is evaporated by the heat of the heater 37c. The evaporated hydrogen peroxide is again liquefied by the temperature reduction until it is led near the bottle 1 through the nozzle 4. Thereby the mist of the hydrogen peroxide which is more detailed than the drop of the hydrogen peroxide is formed in the double fluid spray 35a. By supplying this mist of hydrogen peroxide into the bottle 1, the internal surface of the bottle 1 contacts a hydrogen peroxide, and is sterilized. In addition, the coating weight of the mist of the hydrogen-peroxide to one bottle with a capacity of 500 ml is converted into a hydrogen-peroxide solution 35% of the weight, and its range of 5 $\mu l$–100 $\mu l$ is desirable. That is, it is desirable to set up the amount of the mist so that the hydrogen peroxide equivalent to the case of supplying the hydrogen-peroxide solution in a bottle which contained the hydrogen peroxide 35% of the weight in the range of 5 $\mu l$–100 $\mu l$ may put on the bottle 1. The range in 0.1 second–1 second is desirable for the supplying time of the mist for a bottle. Over 35% of the weight is desirable for the concentration of hydrogen peroxide which is included in formed mist. The disinfectant can use not only hydrogen peroxide but various kind of chemicals with the sterilization action.

After supplying the mist, the bottle 1 is conveyed to the step of supplying a hot blast. During conveyance, the bottle 1 is retained the condition that the disinfectant mist was supplied into the inside for a prescribed time. At the step of supplying a hot blast, a nozzle 5 is inserted in the bottle 1, and the hot blast is supplied in from the nozzle 5. The bottle 1 is heated by the hot blast from inner surface, and the sterilization effect is improved, while a penetration of the hydrogen peroxide into the bottle 1 is suppressed, and the hydrogen peroxide becomes easy to appear on the internal surface of the bottle 1. Furthermore, the mist which is drifting to the internal space of the bottle 1 is discharged by hot blast out of the bottle 1. At this time, since the internal surface of the bottle 1 has already been sterilized by the disinfectant mist put on the internal surface of the bottle 1, even if the mist which is drifting to the internal space of the bottle 1 is discharged out of the bottle 1, the sterilization effect is not spoiled, but superfluous penetration of the hydrogen peroxide to the internal surface of the bottle 1 is suppressed by discharging excessive mist at an early stage rather, and the advantage that finished rinsing for a short time is performed in a post step.

The range of 1.0 second–10 second is desirable for the leaving time until it starts the supplying the hot blast after the supplying the disinfectant mist. The supplying the hot blast may be performed within all mist which is drifting to the internal space of the bottle 1 can be discharged out of the bottle 1, and it is sufficient as a time in about 1 second. When the temperature of the hot blast is more than the heat-resistant temperature (for example 60° C.) of the bottle 1, cautions are required. Because the time of supplying the hot blast is so long that the bottle 1 is heated over the heat-resistant temperature, and is deformation, etc. It is desirable that a nozzle 5 is inserted to the transition region 1b of the bottle diameter equal to the step of preheating.

After supplying the hot blast, the bottle 1 is conveyed to the step of rinsing. During conveyance, the bottle 1 is retained the heated condition for a presscribed time. Then, the bottle 1 is inverted top and bottom at the end of conveyance. At the step of rinsing, a nozzle 6 is inserted in the interior of the bottle 1, and the asepsis water which is heated is supplied from the the nozzle 6 as a rinsing fluid. Thereby, hydrogen peroxide which put on the internal surface of the bottle 1 is rinsed. It is desirable that the nozzle 6 is inserted to the transition region 1b of the bottle diameter equal to the step of preheating and the step of supplying the hot blast.

The range of 1.0 second–10 second is desirable for the standing time until it starts the supplying the asepsis water after stopping the supplying the hot blast. Though the asepsis water is an ordinary temperature, its heated is improved the rinsing effect it is desirable. The range of 40° C.–80° C. range is desirable for the temperature of the rinsing fluid. The rinsing by the asepsis water can be finished in the short time, because penetration of the hydrogen peroxide to the bottle 1 is suppressed in the step of supplying the hot blast mentioned above. For example, it can finish for about 3 seconds, if it is 500 ml bottle.

FIG. 4 shows an aseptic packaging system using the method of sterilization mentioned above. This aseptic packaging system has an asepsis chamber 10. In advance of filling up something to drink to the bottle 1, predetermined sterilization process is performed to the interior of the asepsis chamber 10. Then an asepsis air filtered is always supplied in the chamber 10, and a pressure in the chamber 10 is kept to positive pressure (the condition which is higher than the atmospheric pressure).

An installation port 11 and an exhaust port 12 of the bottle 1 are prepared in the asepsis chamber 10. The bottle formed by the bottle forming machine which is not shown is conveyed along a conveyance line 13, is taken in the chamber 10 from the installation port 11, and in addition, is supplied in a machine 15 of sterilization for external surface through a turntable 14. The machine 15 of sterilization for external surface contacts the disinfectant mist (hydrogen peroxide) in external surface of the bottle 1 conveyed by the turntable 15a, and sterilizes external surface of the bottle 1. A preheating zone 15b is prepared in the part in turning oute of turntable 15a, In the zone 15b, the nozzle 2 of FIG. 1(a) Is inserted in the interior of the bottle 1, the nozzle 2 moves with the bottle 1, while it synchronizes with bottle of 1, and the bottle 1 is preheated. In The zone 15b, the nozzle 3 for heating the neck portion 1a, if it is necessary, is also formed.

Next, the bottle 1 which the external surface was sterilized by the machine 15 of sterilization for external surface is conveyed to a turntable 16a of a machine 16 of sterilization for internal surface. A leaving zone 16b is prepared in the part in turning route of turntable 16a, and the bottle 1 is left for the prescribed time by passing the zone 16b. the bottle 1 which passed the leaving zone 16b is conveyed to a sterilization zone 16c for internal surface. At sterilization zone for internal surface 16c, the nozzle 4 (refer to FIG. 1(b)) which supplies the hydrogen peroxide mist is prepared, and the hydrogen peroxide mist is supplied into the bottle 1 from the nozzle 4. The bottle 1 which passed the sterilization zone for internal surface 16c is conveyed to a turntable 17a of a hot blast supplying machine 17.

A leaving zone 17b and a hot blast supplying zone 17c are prepared in the part in turning route of turntable 17a. By passing this leaving zone 17b, the bottle 1 is left in the condition that the hydrogen peroxide mist was supplied to the inside for the prescribed time. At the hot blast supplying zone 17c, the nozzle 5 of FIG. 1(c) is inserted in the interior of the bottle 1, the nozzle 5 moves with the bottle 1, while it synchronizes with bottle of 1, the hot blast is supplied in the bottle 1, and the hydrogen peroxide mist of the inside is discharged.

The bottle 1 which passed the hot blast supplying zone 17c is conveyed to a turntable 19a of a rinsing machine 19 through a turntable 18. In addition, a leaving inversion zone 18a is prepared in the interval to hot blast supplying zone 17c and delivery site of the bottle 1 from the turntables 18 to the rinsing machine 19. By the bottle 1 passing the leaving inversion zone 18a, a predetermined standing time is made in the interval from the hot blast supplying to the rinsing start. Moreover, while passing the leaving inversion zone 18a, the bottle 1 is inverted top and bottom.

The nozzle 6 of FIG. 1 (d) is inserted in the bottle 1 conveyed to turntable 19a of a rinsing machine 19, the nozzle 6 moves with the bottle 1, while it synchronizes with bottle of 1, the asepsis water which is heated is supplied in the bottle, and the inside of the bottle 1 is rinsed.

The bottle 1 rinsed by the rinsing machine 19 is continuously conveyed to a turntable 21a of a filling machine 21 through a group of turntables 20. The drink is filled up in the inside of the bottle 1, while the bottle 1 is conveyed along this turntable 21a. The bottle 1 that the drink was filled up is conveyed to a lid putting machine 22. The lid putting machine 22 thrusts a cap, which is not shown, onto the neck portion 1a of the bottle 1, and seals the bottle 1. In addition, in the lid putting machine 22, the cap which is sterilized by a cap sterilization machine 24 is supplied from the cap-feeder 23 which is set in the exterior of the asepsis chamber 10. The bottle 1 sealed by the lid putting machine 22 is carried out by conveyance line 25 from the exhaust port 12 to the outside of asepsis chamber 10.

Moreover this invention can be carried out in various forms without limiting to the above preferred embodiments. It may perform the independent devices it by discharging of the mist from the bottle 1 and heating of the bottle 1 each. For example, the bottle 1 may be heated by radiant heat from heat source set the outside of it, etc., while the mist is discharged, by drawing the air from the inside of the bottle 1. A exhaust nozzle of hot blast is prepared in the position which faces a neck portion inner surface of nozzle 2, and drum section 1c, etc., may be able to differently heat the neck portion 1a. This invention can be used for the sterilization of various containers without limiting to the beverage bottle 1. The preheating may be omitted. After stopping the supplying the disinfectant mist, supplying the hot blast may be started immediately. After discharging mist by supplying the hot blast, rinsing may be started immediately.

Alternatively, if the container sterilized by this invention is molded by blow molding machine (for example PET bottle, etc.), a preliminary sterilization may be performed in the stage of the preform before blow molding.

A specific example of the preliminary sterilization method is that dropping a hydrogen peroxide solution diluted by volatile solvent in inner surface of the preform, storing the perform in a container, evaporating the hydrogen peroxide solution which is dropped in inner surface of the perform during carrying the container and storing the container, and sterilizing inner surface of the preform by the evaporated hydrogen peroxide steam. Like this, it is possible that the time of sterilization of the container inner surface is shortened in comparison with the hydrogen peroxide water solution by promoting the evaporation rate of hydrogen peroxide, because the coat in which the hydrogen peroxide solution is rapidly thin in preform inner surface in extent and inner surface is formed, by diluting the hydrogen peroxide water solution by the volatile solvent.

Figure 5A:
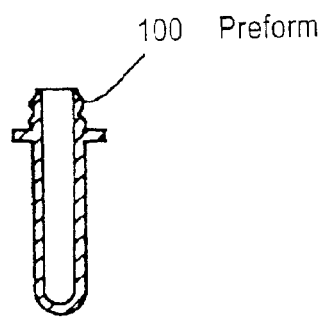
FIG. 5 is a explanatory view showing in the case of the preliminary sterilization.
Figure 5B:
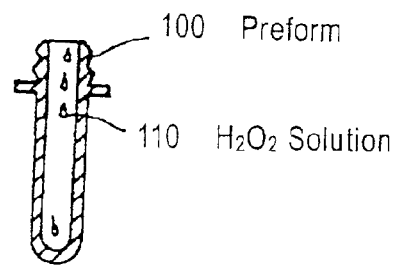
Figure 5C:
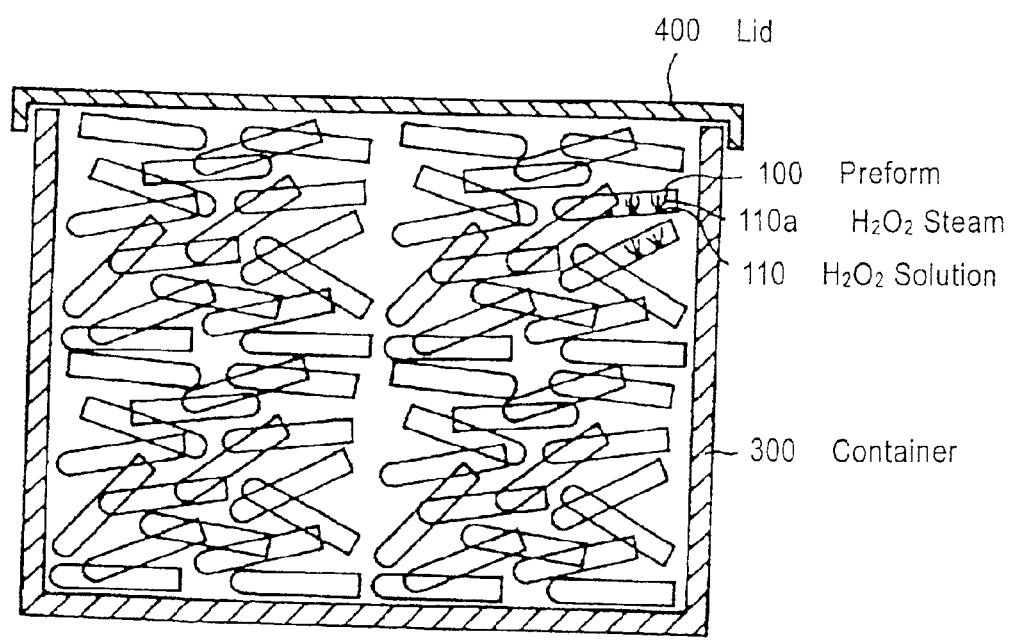

FIG. 5 is an explanatory view showing in the case of the preliminary sterilization. To begin with, a preform 100 shown in FIG. 5(a) is molded using an injection molding machine. In case of the PET bottle, the preform 100 is molded of polyethylene terephthalate resin (hereafter it is called PET resin). The preform 100 may be molded of not only PET resin but nylon and other thermoplastic resin. 35% hydrogen peroxide water solution diluted by volatile solvents such as the ethanol is dropped into the preform 100, shown in FIG. 5(b). The preform 100 dropped $H_2O_2$ solution is put into the container 300, end the container 300 is sealed with a lid 400, shown in FIG. 5(c). The container 300 which is put into the preform 100 is carried to the place for blow molding. $H_2O_2$ solution diluted by the volatile solvent which concentration of hydrogen peroxide $H_2O_2$ is the range of 0.1%–10% is used, about 0.5–5% at the $H_2O_2$ concentration is desirable, when it was diluted by the ethanol. An amount of the $H_2O_2$ solution which is dropped into the preform 100 is different by the dilution solvent, and it is dropped within 0.1–100 $\mu l$. When it was diluted by the ethanol, 1~30 $\mu l$ is desirable. The preform 100 which is dropped the $H_2O_2$ solution is stored into the container 300 with sealed, shown in FIG. 5(c), after that The container 300 which is put into the preform 100 is carried to the place for blow molding, and the preform 100 is molded to a bottle by the blow molding machine. Further then, it is sterilized by the method of this invention mentioned above. The $H_2O_2$ solution dropped in the preform 100 evaporated in the container curing carrying and storing, the $H_2O_2$ steam 110a sterilizes the surface of the perform. That is to say. $H_2O_2$ solution 110 dropped in the preform 100, since the dilution solvent is a volatile solvent, it rapidly evaporates in the preform 100, and it diffuses in the preform 100. At the same time, $H_2O_2$ also evaporates with the dilution solvent, it becomes $H_2O_2$ steam 110a, the $H_2O_2$ steam 110a contacts the inner surface of preform 100, and the inner surface of preform 100 is sterilized. Since the dilution solvent of $H_2O_2$ is a volatile solvent, the evaporation rate of $H_2O_2$ is promoted, it becomes $H_2O_2$ steam 110a in the short time, the density of $H_2O_2$, steam 110a in the preform heightens, and the sterilization effect of inner surface of the preform 100 heightens. And, the $H_2O_2$ steam 110a evaporated in the preform 1 goes on the out side of the preform 1, because a neck portion of the preform 1 is opened. But the 202 steam 110a fills up into the container, and sterilized the outside of the preform 1, because the container 300 is sealed with a lid 400.

Like this, by the preliminary sterilization, the pollution level by the microorganism decreases on the bottle which was molded by blow molding machine very much, and it is possible that sterilization efficiency and operation performance in the case of the method of this invention are improved.

Still, this preliminary sterilization method can apply not only the container which is moiled by blow molding machine like plastics mold container, but paper container. And, as the dilution solvent mentioned above, it may be used that can dissolve hydrogen peroxide or hydrogen peroxide water solution, and has volatility, for example, ethanol, methanol, acetone, isopropyl alcohol, etc., if it is a solvent with the volatility, or the mixture of volatile solvent. Especially, the ethanol is excellent of the handling of compatibility with the hydrogen peroxide water solution, wettability to plastic material, permeabilities, evaporation rates, etc., and it is more suitable. By using the volatile solvent as dilution solvent of the hydrogen peroxide water solution, hydrogen peroxide solution dropped in the container forms the coat which is thin in container inner surface, evaporation rate is promoted, the steam pressure of hydrogen peroxide heightens, and the sterilization efficiency, it is possible to shorten the time of the sterilization of the container.

EXAMPLE

Sterilization process was performed, changing the conditions of a detail according to the following procedure for PET bottle (bottle made from a polyethylene terephthalate) with a capacity of 500 ml.

1. The hot blast 3 was supplied to the interior of the bottle per minute 0.1 m from the nozzle with a bore of 10 mm, and the preheating of the bottle was carried out. The temperature of hot blast was set as 105° C.–125° C. near the nose of the nozzle, and the amount of insertions into the bottle of the nozzle was set as 30 mm. Simultaneously, the hot blast of 85° C. was turned and sprayed on the lip portion of a bottle by the flow rate of 3 per minute 0.1 m from the nozzle with a bore of 50 mm. In addition, the number of nozzles for the lip portion heating was two to one bottle. The blasting time of the hot blast from each nozzle was set up in 3 seconds. The temperature in the bottle after the hot blast supplying had reached 50° C.

2. The bottle was left for 1 second after the hot blast supplying, and hydrogen peroxide mist was continuously blown for 0.6 seconds into the bottle. The coating weight to the internal surface of the bottle of a hydrogen peroxide was converted into the hydrogen-peroxide solution 35% of the weight, and was taken as 15–40 $\mu l$.

3. The bottle was left for 0.5–3.5 seconds after the mist supplying. Then, the nozzle was inserted into the bottle and hot blast was blown for 1 second. The bore of the nozzle, the amount of insertions of the nozzle, and the temperature and the flow rate of the hot blast were the same as the preheating.

4. The bottle was left for 1–3.5 second after hot blast blowing in. Then, the bottle was inverted and was inserted the a nozzle a nozzle with a bore of 6 mm in the interior, and the bottle was rinsed for aseptic water which is heated by 70° C. for 3 seconds. The flow rate of aseptic water was 8.5 L/min.

Moreover, a part of process was omitted when sterilization process was performed.

About each of each sterilization conditions, five bottles with the *Bacillus subtilis* spore of 103, 104, and 105 was sterilized, the trypto-soy bouillon medium was distributed aseptically in the bottle, and the existence of culture and sterilization was evaluated. The bacterial number of survivals was computed by the most probable number (MPN: most probable number) in probability theory from the test result in each sterilization conditions, and the following formula estimated the sterilization effect in quest of the opposite numeric value of the number of adhesion *bacilli*, and the number of survival *bacilli*.

Equation 1

Sterilization effect=log (the number of adhesion *bacilli*/ the number of survival *bacilli*). The list of test results is shown in the following table.

is the same, and the existence of a preheating differs. These results show that it is high sterilization effect to supply hydrogen peroxide mist after preheating. However, if the leaving time after supplying mist is lengthened, the sterilization effect will be improved to practically sufficient level.

When the condition 2 is compared with the condition 8, or the condition 3 is compared with the condition 9, it turns out that the sterilization effect is spoiled. Because the amount of residual of a hydrogen peroxide or the coating weight of hydrogen peroxide mist is the same, but the leaving time until it will start supplying the hot blast after supplying hydrogen peroxide mist in the bottle.

At the condition 10 and 11, the hot blast supplying after the mist supplying is omitted. When the condition 3 is compared with the condition 10, even when the coating weight of hydrogen peroxide mist is the same, when the hot blast supplying is omitted, it turns out that the residual concentration of a hydrogen peroxide rises. When the condition 2 is compared with the condition 11, when the residual concentration of hydrogen peroxide mist is the same, when a hot blast supplying is omitted, it turns out that the sterilization effect run short.

In order to see the effect of heating of the neck portion of the bottle in the step of preheating, at the condition 3, the neck portion was not heated from the outside, but the neck portion of a bottle was heated from the exterior at condition 5. If the neck portion is independently heated so that clearly from these comparisons, the sterilization effect will go up.

As explained above, according to the sterilization method of this invention, the penetration of the disinfectant compo-

TABLE 1

| | Preheating (° C.) | Amount of mist (μl) | Leaving time (sec) | Supplying hot blast | Standing time (sec) | Rinsing time (sec) | Residual concentration (ppm) | Sterilization effect | Remains judgment | Sterilization judgment | Comprehensive judgment |
|---|---|---|---|---|---|---|---|---|---|---|---|
| Condition 1 | 50 | 35 | 3.5 | Yes | 1.0 | 3 | 0.8 | 6.5 | X | ○ | Δ |
| Condition 2 | 50 | 25 | 3.5 | Yes | 1.0 | 3 | 0.5 | 5.5 | ○ | ○ | ○ |
| Condition 3 | 50 | 20 | 3.5 | Yes | 1.0 | 3 | 0.4 | 5.0 | ○ | ○ | ○ |
| Condition 4 | 50 | 15 | 3.5 | Yes | 1.0 | 3 | 0.3 | 4.5 | ○ | ○ | ○ |
| Condition 5 | 50 | 20 | 3.5 | Yes | 1.0 | 3 | 0.4 | 5.5 | ○ | ○ | ○ |
| Condition 6 | No | 40 | 3.5 | Yes | 1.0 | 3 | 0.5 | 3.0 | ○ | X | X |
| Condition 7 | No | 20 | 3.5 | Yes | 1.0 | 3 | 0.2 | <2 | ○ | X | X |
| Condition 8 | 50 | 30 | 0.5 | Yes | 3.5 | 3 | 0.5 | 3.0 | ○ | X | X |
| Condition 9 | 50 | 20 | 0.5 | Yes | 3.5 | 3 | 0.2 | <2 | ○ | X | X |
| Condition 10 | 50 | 20 | 3.5 | No | 1.0 | 3 | 0.6 | 4.0 | X | X | X |
| Condition 11 | 50 | 15 | 3.5 | No | 1.0 | 3 | 0.5 | 3.0 | ○ | X | X |

A note: Leaving time is defined as a set time after supplying the mist, berore starting to supply the hot blast;
Standing time is defined as a set time after supplying the hot blast before starting to rinse.
Residual concentration is defined as a residual concentration of hydrogen peroxide into the container rinsed.

In addition, a residual judgment, a sterilization judgment, and a comprehensive judgment are divided into four phases, respectively, and are evaluated, and, ○, Δ, and x show them sequentially from the best thing.

The following point can be checked from the above table.

The condition 3 and the condition 7 have the same coating weight of hydrogen peroxide mist, and the existence of the preheating differs. Moreover, at the condition 2 and the condition 6, the residual concentration of hydrogen peroxide nent to the container is suppressed, while the sterilization effect by mist is improved, by heating the container with which disinfectant mist was supplied, and equipment, since the disinfectant mist which is drifting in the container is obligatory discharged, the penetration of the disinfectant component to the container is effectively suppressed. After that, since the container is rinsed, and the disinfectant adsorbed and permeated the container is rinsed, the residual concentration of the disinfectant is suppressed to to the degree of minimum, and the internal surface of the container can be sterilized certainly for a short time.

Moreover, since according to the heating treatment for the container of this invention the neck portion is heated independently and the whole container can be heated certainly and quickly to desired temperature, it can contribute to improvement in the speed of the sterilization process by using it at the step of preheating in the sterilization method of this invention.

The entire disclosure of JP-A-2001-39414 published on 13th of Feb. 2001 and JP-A-2001–39414 published on 28th of Nov. 2000, including the specification, claims, drawings and summary is incorporated herein by reference in its entirety.

What is claimed is:

1. A method for sterilizing a bottle comprising the following steps in sequence:
   a) preheating the bottle to a temperature of at least 40° C., wherein the step of preheating comprises the steps of
      i) preheating the entire bottle from a first source applying heat to the interior of the bottle, and
      ii) separately preheating the neck portion of the bottle by applying heat from a second source to an exterior surface of the neck portion;
   b) supplying a disinfectant mist to the interior of the bottle;
   c) heating the bottle into which the disinfectant mist has been supplied;
   d) discharging the disinfectant mist from the bottle; and
   d) rinsing the inside of the bottle after discharging the disinfectant mist therefrom.

2. The method as claimed in claim 1, further comprising providing a predetermined waiting period between the steps of supplying the disinfectant mist to the bottle and discharging the disinfectant mist from the bottle.

3. The method as claimed in claim 1, further comprising providing a predetermined waiting period between the steps of discharging the disinfectant mist from the bottle and rinsing the inside of the bottle.

4. The method as claimed in claim 1, wherein a blast of hot air is supplied into the bottle into which the mist has been supplied so as to achieve both the heating of the bottle and the discharging of the disinfectant mist.

5. The method as claimed in claim 1, wherein the step of rinsing the inside of the bottle comprises supplying a heated rinsing fluid into the bottle.

6. The method as claimed in claim 1, wherein the step of preheating the bottle comprises supplying a hot air blast from the first and second sources of heat.

* * * * *